United States Patent
Seyler

(10) Patent No.: US 8,415,524 B2
(45) Date of Patent: *Apr. 9, 2013

(54) THREE-DIMENSIONAL APERTURED FILM FOR TRANSMITTING DYNAMICALLY-DEPOSITED AND STATICALLY RETAINED FLUIDS

(75) Inventor: Rickey J. Seyler, Chesterfield, VA (US)

(73) Assignee: Tredegar Film Products Corporation, Richmond, VA (US)

( * ) Notice: Subject to any disclaimer, the term of this patent is extended or adjusted under 35 U.S.C. 154(b) by 425 days.

This patent is subject to a terminal disclaimer.

(21) Appl. No.: 12/316,323

(22) Filed: Jan. 29, 2009

(65) Prior Publication Data

US 2009/0182295 A1 Jul. 16, 2009

Related U.S. Application Data

(63) Continuation of application No. 11/559,601, filed on Nov. 14, 2006, now Pat. No. 7,518,032.

(51) Int. Cl.
*A61F 13/15* (2006.01)
(52) U.S. Cl.
USPC .......................................... 604/383; 428/131
(58) Field of Classification Search .................. 604/383; 428/132, 131
See application file for complete search history.

(56) References Cited

U.S. PATENT DOCUMENTS

| | | | |
|---|---|---|---|
| 3,945,386 A | 3/1976 | Anczurowski | |
| 3,967,623 A | 7/1976 | Butterworth | |
| 4,323,069 A | 4/1982 | Ahr | |
| 4,324,247 A | 4/1982 | Aziz | |
| 4,609,518 A * | 9/1986 | Curro et al. | 264/504 |
| 4,726,976 A | 2/1988 | Karami | |
| 5,171,238 A | 12/1992 | Kajander | |
| 5,342,334 A | 8/1994 | Thompson | |
| 5,352,217 A | 10/1994 | Curro | |
| 5,368,909 A | 11/1994 | Langdon | |
| 5,439,458 A | 8/1995 | Noel | |
| 5,509,915 A | 4/1996 | Hanson | |
| 5,603,707 A | 2/1997 | Trombetta | |
| 5,614,283 A | 3/1997 | Potnis | |
| 5,643,240 A | 7/1997 | Jackson | |
| 5,846,230 A | 12/1998 | Osborn, III | |
| 6,090,089 A * | 7/2000 | Tsuji et al. | 604/385.01 |
| 6,468,626 B1 | 10/2002 | Takai et al. | |
| 7,402,723 B2 * | 7/2008 | Stone et al. | 604/378 |
| 7,521,588 B2 * | 4/2009 | Stone et al. | 604/378 |
| 2003/0195487 A1 * | 10/2003 | Thomas | 604/385.01 |
| 2004/0043189 A1 | 3/2004 | Huang | |
| 2004/0122395 A1 * | 6/2004 | Stone et al. | 604/383 |
| 2004/0161586 A1 | 8/2004 | Cree et al. | |
| 2005/0027270 A1 * | 2/2005 | Cree et al. | 604/383 |
| 2005/0148970 A1 * | 7/2005 | Kudo et al. | 604/378 |
| 2005/0209575 A1 * | 9/2005 | Stone et al. | 604/383 |
| 2008/0114317 A1 | 5/2008 | Seyler | |

* cited by examiner

*Primary Examiner* — Susan Su
(74) *Attorney, Agent, or Firm* — Condo Roccia LLP

(57) ABSTRACT

A three-dimensional film for use as an acquisition distribution layer in an absorbent article comprising a first surface with drains extending downward from the first surface, the drains being capable of transmitting fluid by gravity; and protrusions extending upward from the first surface to an upper surface with at least one capillary extending downward from the upper surface, the capillaries being capable of transmitting fluid in contact with the upper surface by capillary action. The drains rapidly transmit fluid through the film, particularly fluid that is dynamically-deposited. The capillaries transmit statically-retained fluid that is in contact with the upper surface of the protrusions.

17 Claims, 5 Drawing Sheets

THREE-DIMENSIONAL APERTURED FILM FOR TRANSMITTING DYNAMICALLY-DEPOSITED AND STATICALLY RETAINED FLUIDS

FIELD OF INVENTION

The present invention relates, generally, to a three-dimensional apertured film for use as an acquisition distribution layer in an absorbent article. More specifically, the invention relates to a three-dimensional apertured film for transmitting both dynamically-deposited and statically-retained fluids to an absorbent core of an absorbent article.

BACKGROUND OF INVENTION

Absorbent articles for absorbing body fluids are well known. These articles typically comprise an absorbent core covered by a topsheet, which is positioned adjacent to, and, in use, may contact the user's skin. The topsheet for use in an absorbent article is typically an apertured film, nonwoven, or laminated combinations thereof. Examples of such absorbent articles include diapers, incontinent articles, and sanitary napkins.

One problem associated with absorbent articles is maintaining the dryness of the wearer-facing surface of the topsheet. Generally, when the wearer-facing surface is kept dry, the absorbent article is more comfortable. To maintain a dry wearer-facing surface, the absorbent article should be able to eliminate both dynamically-deposited and statically-retained fluids from the topsheet. Dynamically-deposited fluids are generally voluminous fluids expelled by the user, while statically-retained fluids are residual fluids held in or on the topsheet by surface tension. Each presents different problems. On one hand, dynamically-deposited fluids must be rapidly transmitted to the absorbent core to minimize wearer discomfort and to prevent the lateral runoff of fluids leading to leakage and garment soiling. This rapid transmission of dynamically-deposited fluids by the topsheet to the absorbent core is at a rate greater than the absorbent rate of the core. This causes pooling of unabsorbed fluid on the core surface and leads to higher levels of statically-retained fluid over a larger area of the topsheet. Regardless of the cause, the presence of these statically-retained fluids results in a highly uncomfortable and undesirable sensation.

Eliminating these two types of fluids from the topsheet typically requires two different, and often competing, mechanisms. For example, to remove statically-retained fluid from the surface of an absorbent article, one approach has been to interpose an additional layer, such as a nonwoven, between a nonwoven topsheet and an absorbent core. The interposed nonwoven layer typically has a pore size distribution whose average pore size is smaller than the average pore size of the topsheet. This allows the interposed nonwoven layer to transmit static fluid from the topsheet toward the absorbent core by capillary action. Although this may be effective for removing statically-retained fluids, the smaller average pore size in the interposed nonwoven layer interferes with the rapid transmission of dynamically-deposited fluids to the underlying absorbent core. While this has some benefit as it slows transmission to the core and can prevent fluid from accumulating on the core surface, this leads to fluid accumulating in the interposed nonwoven layer and can lead to fluid accumulation on or in the topsheet or even to leakage from the edges of the absorbent article. Additionally, if the absorbent core becomes saturated, the interposed nonwoven layer can wick moisture in the reverse direction toward the topsheet especially when the article is being compressed.

To handle dynamically-deposited fluids, one approach involves interposing a perforated thermoplastic film such as described in U.S. Pat. No. 6,700,036 between a nonwoven topsheet and an absorbent core of an absorbent article. The film rapidly transmits dynamically-deposited fluid from the topsheet and tends to disperse the fluids to the core area beyond the primary insult zone. This approach, however, is faced with a number of drawbacks stemming from the film's segregation of the topsheet and core. For example, any fluid that does not penetrate the film to be absorbed in the core may be wicked up by the topsheet to the wearer-facing surface. Furthermore, the film traps moisture in the nonwoven topsheet since it blocks the core from wicking moisture away from the topsheet by interrupting the capillary gradient. Although films with capillary-sized apertures are known for use as topsheets, see, for example, U.S. Pat. No. 4,637,819, their effectiveness in removing residual fluid from a nonwoven topsheet is questionable since they would seemingly lack sufficient contact with the topsheet. These apertured films further suffer from their inability to rapidly transmit the dynamically-deposited fluid to the core and to provide sufficient core-side volume space to disperse the fluid to areas of unsaturated core.

Other approaches for eliminating statically-retained fluid include using an apertured formed film as a topsheet. A problem with this approach is that there is a considerable upper surface area which does not allow passage of fluid through the film to an absorbent core below. This upper surface can remain wet, particularly if this surface is hydrophilic. This wetness can cause the film to adhere to the wearer's skin when brought into contact during use. Another problem with this approach is that some consumers do not like the plastic feel associated with formed films.

Therefore, there is a need for an absorbent article that can transmit both dynamically-deposited fluids and statically-retained fluids. The present invention fulfills these needs among others.

SUMMARY OF THE INVENTION

The present invention relates to an absorbent article that is able to optimize the transmission of both dynamically-deposited fluids and statically-retained fluids. Specifically, the present invention relates to a three-dimensional apertured film for use as an acquisition distribution layer in an absorbent article. The film has one set of relatively-large apertures, or drains, which transmit dynamically-deposited fluids from a topsheet to an absorbent core by gravity, and another set of smaller apertures, or capillaries, which are configured to contact the topsheet and draw statically-retained fluids away by capillary action. In a preferred embodiment, the film transmits dynamically-deposited fluids at a controlled rate using drains in conjunction with basins that are able to collect and temporarily hold fluid before transmitting such fluid to the core. This gives the absorbent core more time to absorb the fluid and reduces the likelihood of fluid rewetting the topsheet. Also in a preferred embodiment, the film comprises one or more protrusions on which the capillaries are located such that they contact or protrude into the topsheet to allow the capillaries to wick away moisture. Additionally, the protrusions create additional void space between the topsheet and core, thereby facilitating lateral flow of dynamically-deposited fluids from a saturated core area to an unsaturated area.

Accordingly, one aspect of the invention is a three-dimensional film having drains to facilitate fluid flow by gravity and capillaries, which are configured to contact a nonwoven topsheet of an absorbent article to facilitate fluid flow by capillary action. In a preferred embodiment, the film comprises a first surface with drains extending downward from the first surface and being capable of transmitting fluid by gravity; and protrusions extending upward from the first surface to an upper surface with at least one capillary extending downward from the upper surface, the capillaries being capable of transmitting fluid in contact with the upper surface by capillary action. As mentioned above, the drains rapidly transmit fluid through the film, particularly fluid that is dynamically-deposited. The capillaries transmit fluid that is in contact with the upper surface of the protrusions including fluid that would otherwise be statically-retained.

Another aspect of the invention is an absorbent article having an acquisition distribution layer comprising a film with drains to facilitate transmission of fluids by gravity, and with capillaries physically contacting a topsheet to draw fluid from the topsheet through capillary action. In a preferred embodiment, the article comprises: a nonwoven topsheet having an upper and lower surface; an absorbent core; and a three-dimensional film between the topsheet and the absorbent core comprising at least: a first surface, drains extending downward from the first surface and being capable of transmitting fluid by gravity; and capillaries contacting the topsheet and extending downward from the topsheet, the capillaries being capable of drawing fluid from the topsheet by capillary action. In use, the drains of the three-dimensional film of the absorbent article can rapidly transmit fluid dynamically-deposited on the topsheet to the absorbent core. On the other hand, the capillaries of the three-dimensional film can transmit static fluid from the topsheet. The capillaries are preferably contained on protrusions that extend upward from a primary plane of the film. The upper surfaces of these protrusions may be in the same or different planes. These protrusions may be in contact with the lower surface of the topsheet or may extend into the topsheet. By varying the extent in which the protrusions extend into the topsheet, static fluid from all areas of the topsheet may be removed by the capillary action of the capillaries.

DETAILED DESCRIPTION

Figure 1:
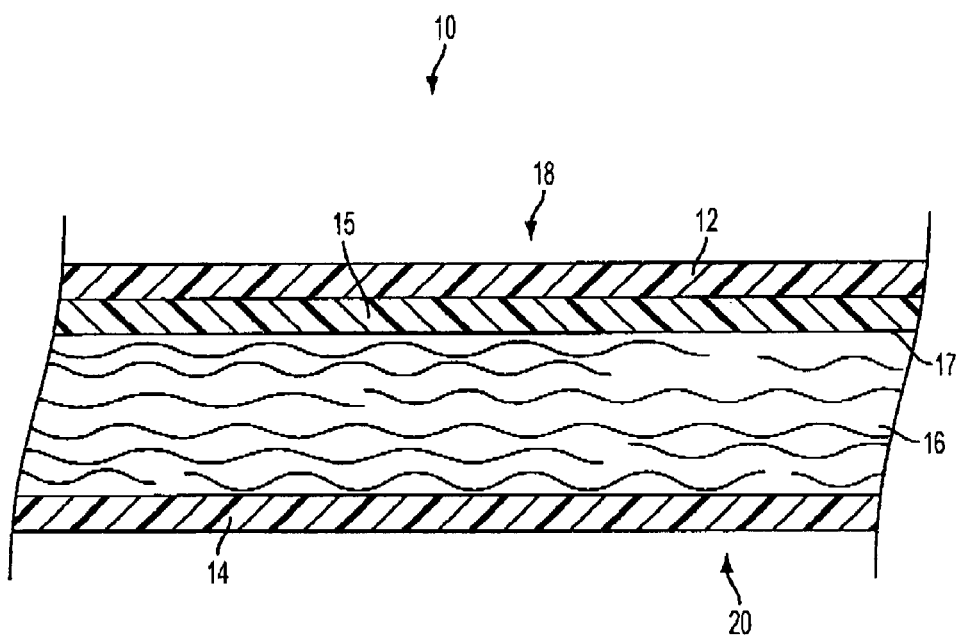
FIG. 1 shows a cross-sectional view of a schematic of an absorbent article that utilizes applicant's three-dimensional film.

Referring to FIG. 1, a simplified representation of a typical absorbent article 10 is shown. Examples of absorbent articles include diapers, incontinent articles, sanitary napkins, and similar articles. It should be understood, however, that FIG. 1 is shown for purposes of example only, and should not be construed to limit the particular type or configuration of absorbent article. As shown in FIG. 1, the absorbent article 10 has two surfaces, a wearer-facing surface or wearer surface 18 and a garment-facing surface or garment surface 20. The wearer surface 18 is intended to be worn adjacent to the body of the wearer. The garment surface 20 of the absorbent article 10 is on the opposite side and is intended to be placed adjacent to the wearer's undergarments or clothing when the absorbent article 10 is worn. The absorbent article 10 basically comprises topsheet 12, acquisition distribution layer 15, absorbent core 16, and a backsheet 14. Other layers may be included in this general construction.

Figure 2:
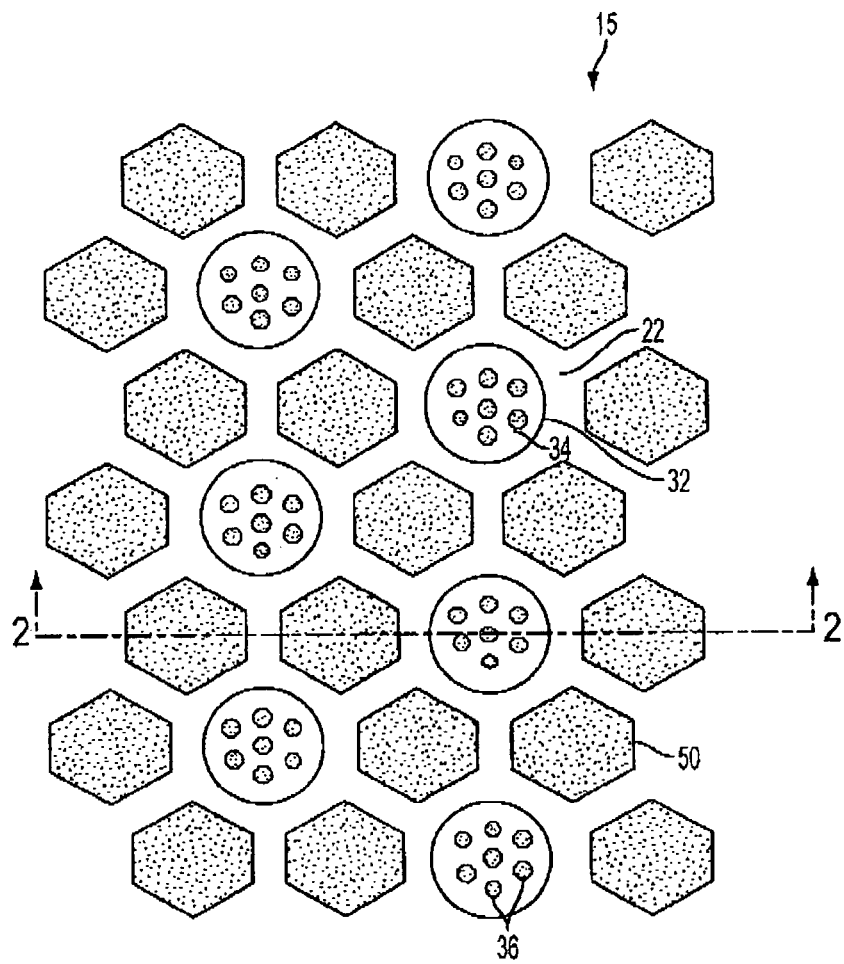
FIG. 2 shows a plan view of a first embodiment of applicant's three-dimensional film for use as an acquisition distribution layer in the absorbent article of FIG. 1.
Figure 3:
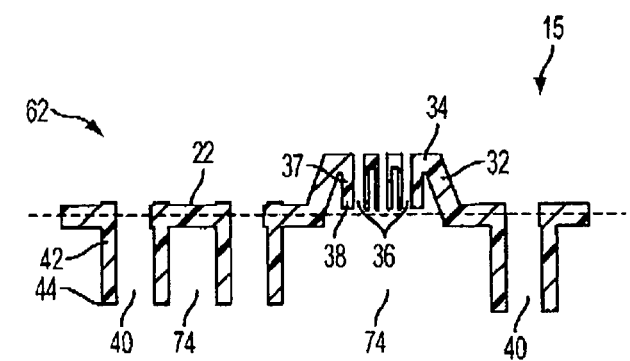
FIG. 3 shows a cross-sectional view of the first embodiment of the three-dimensional film of FIG. 2 taken along line 2-2 of FIG. 2.

The present invention relates, generally, to a three-dimensional apertured film for use as an acquisition distribution layer 15 in an absorbent article 10. Referring now to FIGS. 2 and 3, the three-dimensional film comprises a first surface 22 with drains 40 (FIG. 3) extending downward from the first surface 22 and capable of transmitting fluid by gravity; and protrusions 32 extending upward from the first surface 22 to an upper surface 34 with at least one capillary 36 extending downward from the upper surface 34, the capillary 36 being capable of transmitting fluid in contact with the upper surface 34 by capillary action. Throughout the remainder of this application, similar components will share the same numbers for all embodiments of the invention.

In a preferred embodiment, the first surface 22 is imparted with a hexagonal pattern. Although a hexagonal pattern is used for purposes of illustration, it should be understood that other patterns may also be used for any of the films described herein. Examples of other patterns include circular, oval, elliptical, polygonal, or other suitable patterns or combinations of patterns. The hexagonal pattern forms a plurality of adjacent hexagons or cells 50.

In a preferred embodiment, the hexagonal pattern is based on an 11 mesh wherein "mesh" is the number of cells 50 aligned in a one-inch length. Although a mesh count of about 11 is preferred, a mesh count of from about 2 to about 25 or more preferably from about 4 to about 15 may be used. Preferably at least 50% of the cells, and more preferably at least 70%, of the cells 50 are provided with a drain 40 that has a diameter which is large enough to allow insult fluids to be acquired through the three-dimensional film 15 by gravity and as rapidly as the fluids are delivered.

In this embodiment, the remaining cells are provided with a single protrusion 32 having an upper surface 34 and capillaries 36 extending downward from the upper surface 34. Each protrusion contains preferably about 2 to about 10 capillaries, and more preferably about 3 to about 5 capillaries. The capillaries are sized such that the capillaries exhibit capillary action and thus are able to transmit fluid in contact with the upper surface 34 of the protrusions 32.

As seen more clearly in FIG. 3, which shows an enlarged cross sectional view of film 15 taken along line 2-2 of FIG. 2, the three-dimensional film 15 has a male side or garment-facing side 64 and an opposite female side or wearer-facing side 62. The distance from the first surface 22 of the film to the upper surface 34 of the protrusions 32 is about 50 microns to about 300 microns, more preferably about 100 microns to about 250 microns, and most preferably about 200 microns. Although FIG. 3 depicts the upper surface 34 of the protrusions 32 in a common plane, the upper surfaces 34 of the protrusions 32 can lie in different planes. The distance from the first surface 22 of the film to bottom of the drain 40 is about 800 microns to about 1400 microns, more preferably about 900 microns to about 1200 microns, and most preferably about 1100 microns.

As can be seen in FIG. 1, when used as an acquisition distribution layer for an absorbent article, the three-dimensional film 15 is located beneath the topsheet 12 and adjacent to the top or wearer-facing side 17 of the absorbent core 16. In a preferred embodiment, the topsheet comprises any nonwoven web of individual fibers or threads which are interlaid, but not in any regular, repeating manner. Any nonwoven web commonly known in that art as suitable for topsheet applications can be used. Nonwoven webs have been, in the past, formed by a variety of processes such as, for example, meltblowing processes, spunbonding process, and bonded carded web processes.

Referring to FIG. 3, the first surface 22 of the film is a three-dimensional structure having a plurality of drains 40, each of which has a base opening 42 and an apex opening 44. Preferably, the drains 40 are tapered in the direction of the apex opening 44. The tapered drains decrease the likelihood that fluid will be transmitted through the film from the garment-facing side 64 to the wearer-facing side 62. The apex openings 44 of the drains 40 are in intimate contact with the absorbent core 16 (FIG. 1), and preferably apex openings 44 are affixed to core 16 (FIG. 1) to ensure this intimate contact. It should also be noted that essentially only the apex openings 44 of the drains 40 are in intimate contact with the core 16 (FIG. 1), thereby ensuring that the void spaces 74 providing for lateral spillage remain substantially unencumbered.

As seen in FIG. 3, protrusions 32 extend upward from the first surface 22 to an upper surface 34. The upper surface 34 of the protrusions 32 come in contact with the lower surface of the topsheet 12 or extend into the topsheet 12. The protrusions 32 preferably have a plurality of capillaries 36, each of which has a base opening 37 at the upper surface 34 of the protrusion 32 and an apex opening 38. The apex openings 38 of the capillaries preferably do not come in contact with absorbent core 16. By ensuring that the capillaries 36 do not contact the absorbent core, this decreases the likelihood that the capillaries 36 will wick fluid through the film from the absorbent core 16 to the topsheet 12. Moreover, protrusions 32 create additional void spaces 74 providing additional room for lateral transmission of fluid. In another embodiment of present invention, there are no protrusions in the three-dimensional film and the capillaries are present on the first surface 22 of the three-dimensional film 15. Alternatively, the capillaries are both present on the first surface 22 and the protrusions 32 of the three-dimensional film 15.

As discussed above, drains 40 operate to handle dynamically-deposited fluids, i.e., fluids rapidly deposited onto the first surface 22 of the film are transmitted by the drains 40 to an underlying absorbent core without substantial leakage from the edges of the absorbent article. The drains 40 need not be cylindrical in shape to function in their intended manner as long as they are large enough to allow dynamically-deposited fluids to be acquired through the three-dimensional film 15 as rapidly as the fluids are deposited. The drains 40, however, must be sized and have the proper surface chemistry so that they do not present a barrier for dynamically-deposited fluids. It has been found that drains with a diameter greater than about 500 microns, more preferably greater than about 900 microns, do not present a barrier to fluid flow.

If the drains 40 and/or capillaries 36 do not have a "true" diameter (e.g, they have an oval opening), they should be sized to ensure that they have an equivalent hydraulic diameter (EHD) equal to the respective diameters discussed herein. As used herein, the term equivalent hydraulic diameter is defined by the following equation: EHD=4A/P where A is the area of the irregular aperture and P is the perimeter of the irregular aperture. The equivalent hydraulic diameter is the diameter of a circular aperture having fluid flow characteristics similar to the irregular aperture for which the calculation is being done. See U.S. Pat. No. 4,324,246 which is incorporated herein by reference. Therefore, the term "diameter" as used herein refers to either the apparent diameter or the EHD.

While it is generally desirable that the drains exhibit a relatively large diameter to allow the greatest flow of fluid, the upper limit of the diameter is determined primarily on aesthetic and on the basis of rewet considerations. That is, for drains with relatively large diameters, the film tends to look very stiff and harsh and is not pleasing to the consumer. Likewise, for drains with relatively large diameters, there is a greater likelihood that fluid can be transmitted from the absorbent core (e.g., upon compression) through the film to the topsheet. In a preferred embodiment, the drains 40 have diameters preferably no greater than about 1200 microns, and more preferably no greater than about 1000 microns.

Conversely, the capillaries 36 on the protrusions 32 have a smaller diameter such that they do not function appreciably in dynamic situations to transmit significant quantities of rapidly discharged fluid directly to the underlying absorbent core. Rather, capillaries 36, if properly sized and positioned, can remove static fluid from a topsheet. The capillaries 36 need not be cylindrical to function in the intended manner. They can be either regular or irregular in shape. The capillaries 36, however, must be sized and have the proper surface chemistry so that they exhibit capillary action. It has been found that capillaries with a diameter of less than about 375 microns, more preferably less than about 250 microns will exhibit capillary action.

In a preferred embodiment, the ratio of the diameter of the smallest drain 40 to that of the diameter of the largest capillary 36 is preferably at least about 2, and more preferably at least about 4. These ratios tend to ensure that the three-dimensional film will effectively transmit dynamically-deposited fluids by gravity and remove static fluid from the topsheet by capillary action.

As will be appreciated by those of skill in the art, the density and spacing of the drains 40 and capillaries 36 relative to one another will depend primarily upon the anticipated in use flow conditions. It is also possible in practicing the present invention to combine the functions of the drains 40 and capillaries 36 in a single passageway. Examples might include star-shaped passageway, wherein the points of the star behave in a manner similar to the capillaries 36, while the centrally located portion of the star behaves in a manner similar to the drains 40. These combination passageways could be placed on the first surface 22 and/or on the protrusions 32 of the three-dimensional film 15.

Figure 4:
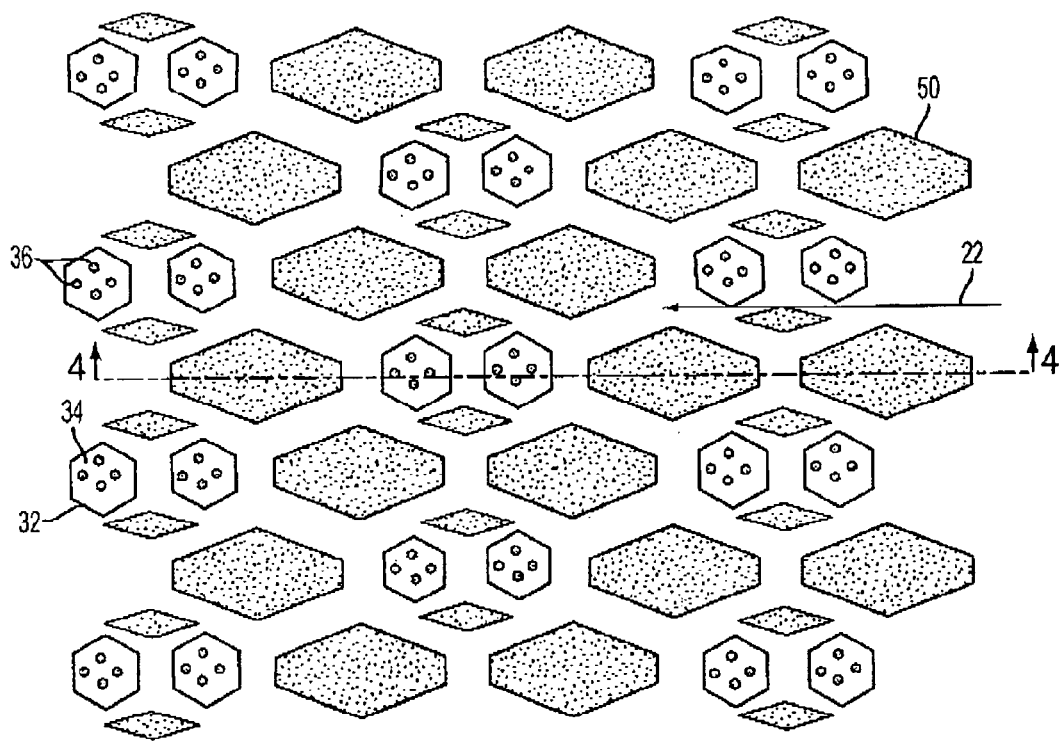
FIG. 4 shows a plan view of a second embodiment of applicant's three-dimensional film for use as an acquisition distribution layer in the absorbent article of FIG. 1.
Figure 5:
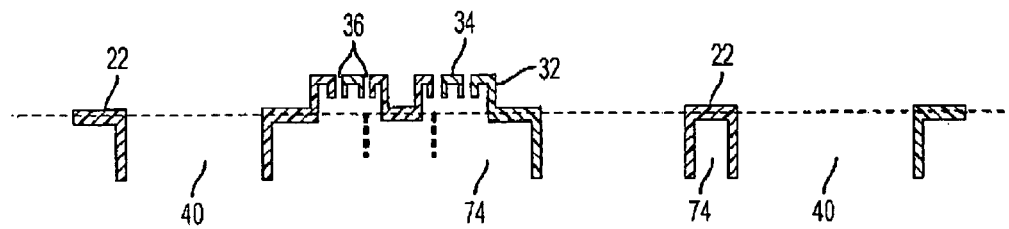
FIG. 5 shows a cross-sectional view of the second embodiment of applicant's three-dimensional film of FIG. 4 taken along line 4-4 of FIG. 4.
Figure 6:
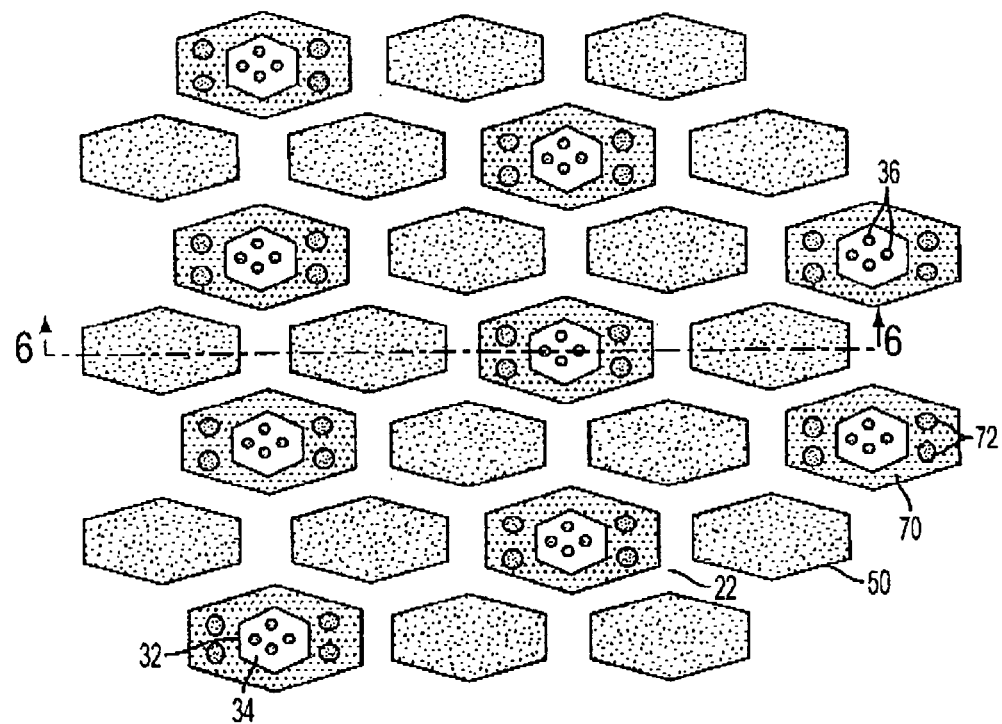
FIG. 6 shows a plan view of a third embodiment of applicant's three-dimensional film for use as an acquisition distribution layer in the absorbent article of FIG. 1.
Figure 7:
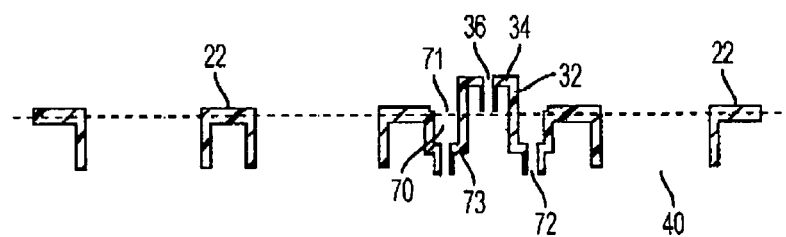
FIG. 7 shows a cross-sectional view of the third embodiment of applicant's three-dimensional film of FIG. 6 taken along line 6-6 of FIG. 6.

FIG. 4 and FIG. 6 show two alternative embodiments of a three-dimensional film of the present invention. FIG. 5 shows a cross-sectional view of the embodiment depicted in FIG. 4. FIG. 7 shows a cross-sectional view of the embodiment depicted in FIG. 6.

In both embodiments, the first surface 22 is imparted with a hexagonal pattern as discussed above. Preferably at least 50% of the cells, and more preferably at least 70%, of the cells 50 are provided with a drain 40 (see FIG. 5 and FIG. 7) that has a diameter which is large enough to allow insult fluids to be acquired through the three-dimensional film 15 as rapidly as the fluids are delivered. The drains 40 are of a size and shape as discussed above with respect to FIGS. 2 and 3.

Referring to the embodiment depicted in FIG. 4 and FIG. 5, the remaining cells are provided with two or more protrusions 32 having an upper surface 34 and capillaries 36 extending downward from the upper surface. The height of the protrusions 32 and the number of the capillaries 36 per protrusion 32 is as discussed above. Although FIG. 5 depicts the upper surface 34 of the protrusions 32 in a common plane, the upper surfaces 34 of the protrusions 32 can lie in different planes. The capillaries are of a size and shape as discussed above such that the capillaries exhibit capillary action and thus are able to transmit fluid in contact with the upper surface 34 of the protrusions 32. Alternatively, the capillaries 36 are additionally present on the first surface 22 of the three-dimensional film 15.

Referring to the embodiment depicted in FIG. 6 and FIG. 7, in addition to protrusions 32, the remaining cells are provided with basins 70 extending downward from the first surface 22. The basins 70 have an upper opening 71 and a bottom 73 with channels 72 extending downward from the bottom of the basins. The height of the protrusions 32 and the number of the capillaries 36 per protrusion 32 is as discussed above. The upper surfaces 34 of the protrusions 32 can lie in the same or different planes. The capillaries are sized as discussed above such that the capillaries exhibit capillary action and thus are able to transmit fluid in contact with the upper surface 34 of the protrusions 32. Alternatively, the capillaries 36 are additionally present on the first surface 22 of the three-dimensional film 15. The distance from the first surface 22 of the film to the bottom 73 of the basins 70 is preferably about 100 microns to about 500 microns, more preferably about 150 microns to about 400 microns, and most preferably about 250 microns.

As discussed above, the basins are capable of collecting and holding fluid and thus function to slow the transmission rate of fluid through the three-dimensional film. The upper openings 71 of the basins 70 have a diameter from about 800 microns to about 1200 microns. In use, as fluid is dynamically-deposited on the topsheet and transmitted to the three-dimensional film, the basins 70 are able to collect and temporarily hold fluid while transmitting the fluid via the channels 72 to the absorbent core 16 (FIG. 1). Because the absorbent core absorbs fluids slower than the rate they are deposited on the absorbent article, the basins function to slow the transmission rate to the absorbent core to give the core more time to absorb such fluids. It has been found that channels 72 with a diameter from about 200 microns to about 500 microns effectively slow the transmission of fluids through the three-dimensional film but allow the basins 70 to drain.

Figure 8:
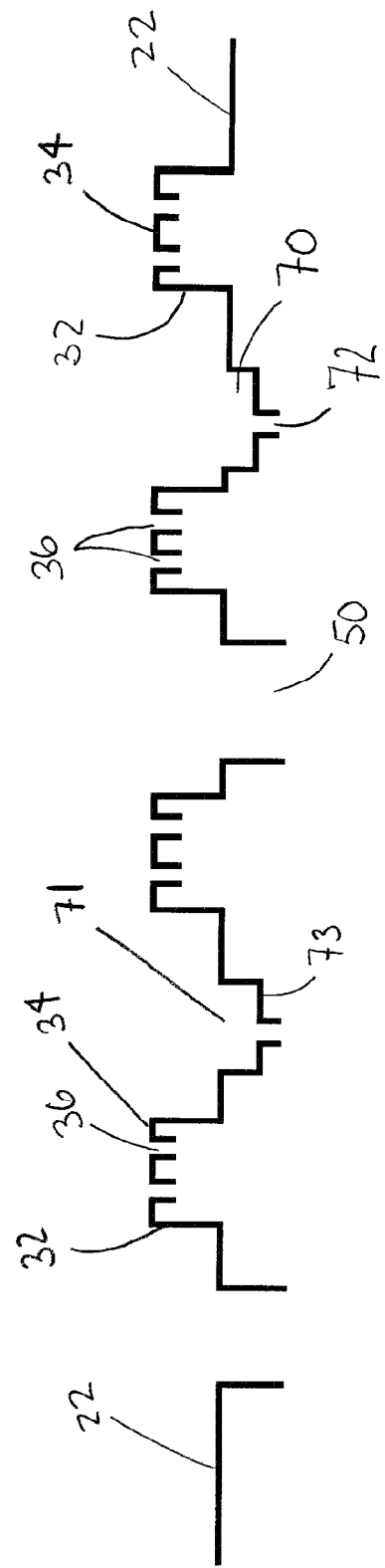
FIG. 8 is a cross-sectional view, similar to FIG. 7, of another embodiment of the three-dimensional film.

In the embodiment depicted in FIG. 6 and FIG. 7, the basins 70 surround the protrusions 32 much like a moat would surround a castle. The basins 70, however, need not surround the protrusions 32 as depicted in FIG. 6. For example, the basins 70 can individually occupy a cell 50 as seen, for example, in FIG. 8. Likewise, when protrusions 32 and basins 70 are both used in a single three-dimensional film, the protrusions can emanate from the first surface 22 of the film (as seen in the embodiment of FIG. 8) or from the bottom of a basin 70 as shown most clearly in FIG. 7. In an alternative embodiment, both the basins 70 and the capillaries 36 could both emanate from the first surface 22 of the film. Alternatively, if the transmission of residual static fluid from the topsheet is not desired, the capillaries 36 could be eliminated from the film.

Preferably, the three-dimensional film 15 is a perforated thermoplastic film which has a run off percent of less than about 10 percent and which has an increased liquid flow rate through the tapered drains. Any thermoplastic material which may be formed into flexible film or sheets may be used in the production of the novel film of the present invention.

Exemplary thermoplastic materials include polyesters, polyamides, vinyl polymers and copolymers, e.g., vinyl acetates, vinyl alcohols, vinyl chlorides; poly methacrylates, poly lactic acid, and polyolefins, e.g., polyethylene, polypropylene, and copolymers or blends thereof which may be formed into flexible film or sheet. Particularly preferred perforated films are polyethylene and polypropylene. One suitable material is a polyethylene film having a thickness of from about 25 microns to about 50 microns. Sheets or film made from such materials may contain additives known in the art to achieve the desired physical characteristics.

When using a hydrophobic thermoplastic material such as a polyolefin resin to form the three-dimensional film, the film is treated so that at least the female or wearer-facing side 62 is hydrophilic. For example, a method of making such a film hydrophilic includes a two-fold surface treatment, which is taught by U.S. Pat. Nos. 4,535,020 and 4,456,570 to Thomas et al. entitled, "Perforated Film" and "Treatment of Perforated Film," respectively, which are incorporated herein by reference. The method teaches that one surface treatment is provided by adding an internal chemical additive, namely a surfactant, to a film forming polyolefin resin. The additive is compounded or otherwise mixed or blended with the resin prior to the film being formed from the resin. After the film is formed the other surface treatment is accomplished by treating the film with a corona discharge treatment which acts on the chemical additive to provide the perforated film with a zero or near zero percent run off. The surfactant provides a film surface which has greater polarizability than the polyolefin film would have without the surfactant being added. Higher surface polarity yields higher wettability. Although the chemically treated film is more polar than untreated film, corona discharge treatment of the film itself provides the desired maximum wettability. Any surfactant which achieves this polarity and which migrates to the surface of the film may be used in this method. A surfactant treatment may also be applied after the film is formed. Alternatively, a non-migrating surfactant or hydrophilic film may be coextruded as a thin "skin" layer on top of the hydrophobic layer.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. A surface is said to be wetted by an aqueous fluid (hydrophilic) when the fluid tends to spread spontaneously across the surface. Conversely, a surface is considered to be "hydrophobic" if the aqueous fluid does not tend to spread spontaneously across the surface.

The three-dimensional apertured films of the type generally shown in FIGS. 2, 3, 4, 5, 6, and 7 can be made by a direct melt vacuum formed film (VFF) process. In the case of a direct melt VFF process, a molten web is extruded onto a forming area of a forming screen. A pressure differential applied across the forming screen causes the molten web to conform to the three-dimensional shape of the forming screen to form cells that ultimately rupture at their tips to become apertures. Alternatively, the web may be reheated and partially melted while the web is over the forming area of the forming screen as taught in U.S. Pat. No. 4,151,240. A melted polymer is desirable to form three-dimensional apertures since a melted polymer is more easily pulled into the apertures in a forming screen. The three-dimensional apertured films of the present invention may also be formed by a hydro-formed film (HFF) process. In a HFF process, hydraulic pressure in the form of water jets impinges upon a solid web as it crosses the forming area of a forming screen. The force of the high-pressure water causes the web to conform to the three-dimensional shape of the forming screen to form cells that ultimately rupture at their tips to become apertures.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A three-dimensional film comprising:
   a first surface with three-dimensional hollow tubular drains extending downward from said first surface and capable of transmitting fluid by gravity; said first surface forming a continuous planar surface wherein any point on said first surface can be accessed from any other point on said first surface without leaving the continuous plane; and
   a plurality of three-dimensional protrusions originating on said first surface and extending upward from said first surface, each protrusion terminating in an upper surface comprising generally planar land areas, said land areas being generally parallel to and spaced from said first surface, said upper surfaces or said protrusions forming a discontinuous planar surface wherein access to any point on one upper surface of any one protrusion from a point on any other upper surface of any other protrusion cannot be accessed without leaving said discontinuous plane; the land areas on each protrusion having at least two three-dimensional capillary structures comprising hollow tubular structures extending downward from said upper surface toward said first surface, capillary structures being capable of transmitting fluid in contact with said upper surface by capillary action.

2. The three-dimensional film of claim 1, wherein at least a portion of said upper surface of said protrusions are approximately in a common plane.

3. The three-dimensional film of claim 1, wherein said upper surface is spaced from about 100 to about 250 microns above said first surface.

4. The three-dimensional film of claim 1, wherein said capillary structures have a diameter less than about 375 microns.

5. The three-dimensional film of claim 1, wherein said drains have a diameter from about 500 microns to about 1000 microns.

6. The three-dimensional film of claim 5, wherein said capillary structures have a diameter at least 4 times smaller than said diameter of said drains.

7. The three-dimensional film of claim 1, further comprising: basins extending downward from said first surface having an upper opening and a bottom forming a second surface, said basins being capable of holding fluid, said second surface having at least one channel extending downward from said second surface and being capable of transmitting fluid by at least one of gravity or capillary action.

8. An absorbent article comprising:
   a nonwoven topsheet having an upper and lower surface;
   an absorbent core; and
   three-dimensional film between said topsheet and said absorbent core comprising a first surface, with three-dimensional hollow tubular drains extending downward from said first surface and being capable of transmitting fluid by gravity; said first surface forming a continuous planar surface wherein any point on said first surface can be accessed from any other point on said first surface without leaving the continuous plane; and a plurality of three-dimensional protrusions originating on said first surface and extending upward from said first surface, each protrusion terminating in an upper surface comprising generally planar land areas, said land areas being generally parallel to and spaced from said first surface, said upper surfaces or said protrusions forming a discontinuous planar surface wherein access to any point on one upper surface of any one protrusion from a point on any other upper surface of any other protrusion cannot be accessed without leaving said discontinuous plane; the land areas on each protrusion having at least two three-dimensional capillary structures comprising hollow tubular structures extending downward from said upper surface toward said first surface, capillary structures being capable of transmitting fluid in contact with said upper surface by capillary action.

9. The absorbent article of claim 8, wherein said capillaries have a diameter less than about 375 microns.

10. The absorbent article of claim 8, wherein said drains have a diameter from about 500 microns to about 1000 microns.

11. The absorbent article of claim 10, wherein said capillaries have a diameter at least 4 times smaller than said diameter of said drains.

12. The absorbent article of claim 8 wherein each protrusion contains 2-10 capillaries.

13. The absorbent article of claim 12, wherein said upper surface of said protrusions is in contact with said lower surface of said topsheet.

14. The absorbent article of claim 12, wherein said protrusions extend into said topsheet.

15. The absorbent article of claim 12, wherein at least a portion of said upper surface of said protrusions are approximately in a common plane, and said common plane is above said lower surface of said topsheet.

16. The absorbent article of claim 12, wherein said upper surface is from about 100 to about 250 microns above said first surface.

17. The absorbent article of claim 8, wherein said three-dimensional film further comprises basins extending downward from said first surface and having an upper opening and a bottom forming a second surface, said basins being capable of holding fluid, said second surface having at least one channel extending downward from said second surface and being capable of transmitting fluid by at least one of gravity or capillary action.

* * * * *